United States Patent [19]

Jarreau et al.

[11] Patent Number: 4,584,289

[45] Date of Patent: Apr. 22, 1986

[54] 14-AMINOSTEROID DERIVATIVES, APPLICATION IN THERAPY AND PROCESS OF PREPARATION

[75] Inventors: Francois-Xavier Jarreau, Versailles; Jean-Jacques Koenig, Vernou la Celle s/Seine, both of France

[73] Assignee: Etablissements Nativelle S.A., France

[21] Appl. No.: 522,957

[22] Filed: Aug. 12, 1983

[30] Foreign Application Priority Data

Aug. 12, 1982 [FR] France .................................. 82 14038
Jun. 17, 1983 [FR] France .................................. 83 10031

[51] Int. Cl.$^4$ ................................................ C07J 5/00
[52] U.S. Cl. .................................. 514/182; 260/397.5; 260/397.1

[58] Field of Search ...................... 260/397.5; 424/238

[56] References Cited

PUBLICATIONS

Chemical Abstracts vol. 86 (1977) Par. 121616q, An article by Astier et al., Bull. Soc. Chim. Fr. 1976, pp. 1581-1582.

Primary Examiner—Elbert L. Roberts
Attorney, Agent, or Firm—Sughrue, Mion, Zinn, Macpeak, and Seas

[57] ABSTRACT

The present invention relates to new 14-aminosteroids and their application in therapy and also to a process for their preparation.

9 Claims, No Drawings

14-AMINOSTEROID DERIVATIVES, APPLICATION IN THERAPY AND PROCESS OF PREPARATION

BACKGROUND OF THE INVENTION

French Patent Application 2,464,270 describes compounds of the 14-aminosteroid type, in particular hydroxylated derivatives of 14-aminoandrostane and of 14-amino-21-norpregnane. Steroid alkaloids of the pregnane and androstane series, substituted in the 14-position by an amino group, are also known; for example, 14β-aminopregnane-3β,20α-diol is described by A. Astier et al., Bull. Soc. Chim. no. 9-10, pages 1581-1582 (1976); other 14β-aminopregnanes and 14β-aminoandrostanes are also described by A. Astier et al., Tetrahedron, Volume 34, pages 1481-1486 (1978). However, neither pharmacological properties nor therapeutic applications have been described for these derivatives.

French Patent Application 2,494,697 describes 3-amino-(5α)-pregnane-17α,20-diol and 3-amino-(5α)-19-norpregnan-20-ol, which are presented as possessing immunotherapeuti properties enabling them to be applied as medicaments for treating autoimmune diseases resulting from a deficiency in certain lymphocytes.

SUMMARY OF THE INVENTION

The studies carried out by the Applicant Company have made it possible to establish, surprisingly, that 14-aminosteroids, and more particularly derivatives of the pregnane-3,20-diol and pregnane-3,12,20-triol type substituted in the 14-position by an amino group, possess positive inotropic properties.

The present invention therefore relates to new medicaments based on 14-aminosteroids, possessing, in particular, a positive inotropic activity enabling them to be applied as cardiotonic medicaments for treating cardiac insufficiencies.

The invention also relates, by way of new products, to 14-aminosteroids of the 14-aminopregnane-3,20-diol, 14-aminopregnane-3,12,20-triol and 14-amino-21-norpregnane-3,12,20-triol series, and also to a process for their preparation.

The new medicaments according to the present invention contain, as active principle, a 14-aminosteroid represented by the general formula (I) below:

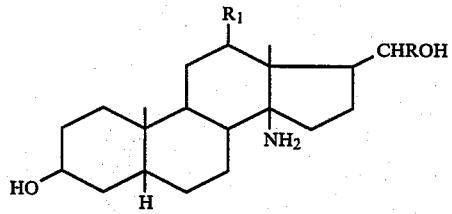

in which R represents a hydrogen atom or a lower alkyl group containing 1 to 4 carbon atoms, for example a methyl group, an ethyl group or an isopropyl group, and $R_1$ represents a hydrogen atom or a hydroxyl group.

The invention also relates to the pharmaceutically acceptable salts of the 14-aminosteroids of the general formula (I), obtained by reaction with a mineral or organic acid in accordance with the methods customary in the art. The acid used can be chosen from amongst hydrochloric acid, oxalic acid, tartaric acid, fumaric acid, lactic acid, phosphoric acid, p-toluenesulfonic acid, formic acid, hydrobromic acid, maleic acid, sulfamic acid and the like.

The invention also relates to the new 14-aminosteroids represented by the general formula (I) above in which R represents a hydrogen atom or a lower alkyl group having 1 to 4 carbon atoms and $R_1$ is a hydrogen atom or a hydroxyl group, R and $R_1$ not being a hydrogen atom simultaneously, and also to their salts with acids.

DETAILED DESCRIPTION OF THE INVENTION

THE 14-aminosteroids of the general formula (I) contain, in their molecule, several asymmetric carbon atoms, in particular the carbons in the 3-, 5-, 14-, 17-and 21- positions, and can therefore exist in various stereoisomeric forms, it being understood that the new compounds according to the invention can be any one of these stereoisomers in the case where $R_1$ is a hydroxyl group, whereas in the case where $R_1$ is a hydrogen atom, they consist of the stereoisomers in which, when the OH group in the 3-position and the $NH_2$ group in the 14-position have the β configuration and when the hydrogen atom in the 17-position possesses the α configuration, irrespective of whether the hydrogen atom in the 5-position has the α or β configuration, the OH group in the 20-position has the β configuration.

The invention relates more particularly to the 14-aminosteroids represented by the general formula (I) above in which R is a methyl group. In this formula, the $—NH_2$ group in the 14-position and the hydrogen atom in the 5-position can have the α or δ configuration, preferably the β configuration. Likewise, the —CHROH group in the 17-position can have the 17α or 17β configuration. The —OH group in the 3-position and the —OH group represented by $R_1$ preferably have the β configuration. When R is not a hydrogen atom, the —OH group in the 20position can have the α or β configuration, and in the case where $R_1$ is a hydrogen atom, it preferably has the β configuration. Of course, the invention relates to these various isomers, in isolation or in a mixture. In accordance with the customary nomenclature, unless otherwise indicated, the hydrogen atoms in the 5- and 17-positions occupy the α configuration in the examples below.

The compounds of the general formula (I) can be prepared from the 3,14-dihydroxysteroids of the general formula (II) below:

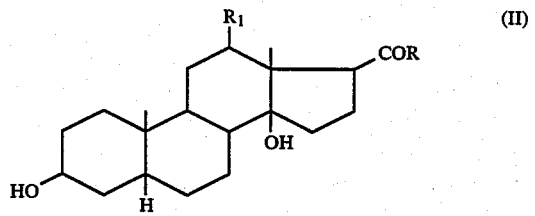

in which R represents a hydrogen atom or a lower alkyl group having 1 to 4 carbon atoms and $R_1$ represents a hydrogen atom or an alkyl group, by means of a reduction reaction followed by an acetylation to form the 3,14,20-trihydroxysteroids 0-acetylated in the 3- and 20-positions, and in the 12-positions when $R_1$ is a hydroxyl group, if the general formula (III) below:

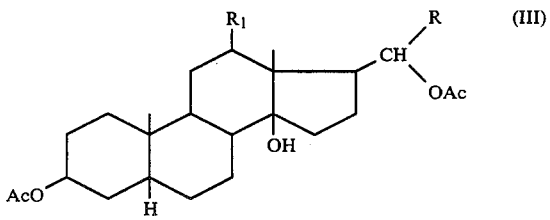

in which R is a hydrogen atom or a lower alkyl group having 1 to 4 carbon atoms, $R_1$ is a hydrogen atom or an acetyl group and Ac is an acetyl group, and by reaction with a hydrazoic acid/boron trifluoride complex to form the corresponding 14-azido derivative, and then by means of a reduction with a metal hydride or by catalytic hydrogenation.

The first step, consisting in carrying out a reduction followed by an acetylation to form a di-0-acetylated trihydroxysteroid when $R_1$ is a hydrogen atom or a tri-0-acetylated tetrahydroxysteroid when $R_1$ is a hydroxyl group, can be carried out, for example, by means of a hydride in accordance with the technique described by J. Fried and J. A. Edwards, "Organic Reactions in Steroid Chemistry", published by Van Nostrand Reinhold (1972). It is possible, for example, to use double hydrides of aluminum or boron, such as sodium borohydride or lithium aluminum hydride, or alternatively other reducing agents such as hydrogen in the presence of catalysts.

the acetylation reaction making it possible to obtain the acetylated steroid of the general formula (III) can be carried out in accordance with the customary techniques, for example by reaction with acetic anhydride in an organic solvent.

In the second step, the derivative of the general formula (III) is converted to the corresponding 14azido derivative by reaction with a solution of a hydrozoic acid/boron trifluoride complex in benzene. The replacement of the hydroxyl group in the 14-position by a tertiary azide group takes place with a good yield, the other hydroxyl groups in the 3-position, 12-position (if appropriate) and 20-position having been protected beforehand by acetylation.

The third step, consisting in converting the 14-azido derivative to the corresponding 14amino derivative, can be carried out by catalytic hydrogenation followed by removal of the acetyl protecting groups, or by reaction with a reducing agent such as a metal hydride, and more particularly lithium aluminum hydride, to form the 14-aminosteroid of the formula (I).

The starting ketones represented by the general formula (II) can be prepared by applying the method described by N. Danielli et al., Tetrahedron, 22, page 3189 (1966). For example, when $R_1$ is a hydroxyl group, a 3,12-diacetoxy-14-hydroxyetianic acid can be treated with an organometallic compound such as methyl-lithium; the reaction can be advantageously be carried out be gradually adding a solution of methyl-lithium in ether, at a temperature below 10° C., to a solution of 3,12-diacetoxy-14-hydroxy-5β-etianic acid in tetrahydrofuran, in the presence of sodium hydride. In the case of the preparation of the derivatives in which R is hydrogen, the reaction can also be carried out directly with a reducing agent such as lithium aluminum hydride. The etianic acid derivative used as the starting material is described in the Literature (D. Taylor, J. Chem. Soc., 1953, page 3325). When $R_1$ is a hydrogen atom, a 3-acetoxy-14hydroxyetianic acid is treated in the same manner with an organometallic compound.

The 14-aminosteroids of the general formula (I) in which R and $R_1$ represent a hydrogen atom can also be prepared by the process described in French Pat. No. 2,464,270. Likewise, the method of preparation described by Astier et al., Bull. Soc. Chin., no. 9–10, pages 1581–1582 (1976) can also be applied in order to obtain the 14-aminosteroids of the general formula (I) in which R is a lower alkyl group and, more precisely, a methyl group.

The process according to the present invention makes it possible to prepare, under satisfactory conditions, the various stereoisomeric forms of the 14-amino-steroid derivatives represented by the general formula (I), in particular the derivatives in which the hydroxyl groups in the 3-position and 12-position (if appropriate) and the hydrogen atom in the 5-position have the β configuration, the amino group in the 14-position preferably possessing the β configuration, while the hydroxyl group in the 20-position can have either the α or β configuration when R is an alkyl group.

The examples described below illustrate the invention without limiting its scope. The structures of the products obtained were verified by their infra-red spectra, NMR spectra and mass spectra.

EXAMPLE 1

(a) Preparation of 3,20-di-0-acetyl-5β-pregnane-3β,14β,20-triol 6 g of 20-oxo-5β-pregnane -3β,14β-diol,obtained by the method of N. Danielli et al. (mentioned above), are dissolved in 30 ml of methanol, 1.5 g of potassium borohydride are then added in portions and the reaction is left to proceed for about 30 minutes. The methanol is removed by evaporation, the residue is extracted with ethyl acetate and the extract is washed. The residue is treated with 16.5 ml of acetic anhydride in 35 ml of pyridine overnight. After hydrolysis and washing with citric acid and water, a residue is obtained (7 g, that is to say a yield of 95%) comprising the two isomers 20α and 20β, which are separated by chromatography on a silica column. (b) Preparation of 14β-amino-5β-pregnane-3β,20α-diol 210 mg of the 20α isomer of the diacetyltriol obtained as indicated above are dissolved in a solution of 16.5 ml of hydrozoic acid in benzene, the mixture is stirred for 5 minutes and 0.4 ml of freshly distilled boron trifluoride etherate reagent is then added. After a reaction time of 10 minutes, the reaction mixture is poured into a mixture of crushed ice and aqueous ammonia solution.

Extraction is carried out with benzene, the extract is washed and dried, the residue is then dissolved in 20 ml of tetrahydrofuran, and 54 mg of lithium aluminum hydride are added. After heating under reflux for 1 hour, the mixture is hydrolyzed and a neutral fraction of 80 mg and a basic fraction of 77 mg of aminopregnanediol (yield 49%) are extracted. Melting point m.p.=258° C.

EXAMPLE 2

14β-Amino-5β-pregnane-3β,20β-diol 9 g of the 20β isomer of the diacetyltriol prepared as indicated in Example 1 a) are dissolved in 600 ml of a benzene solution of hydrozoic acid and the boron trifluoride etherate is then added after a reaction time of 5 minutes, the same treatment as in Example 1 B) being carried out.

This gives 2.3 g of 14-amino-5β-pregnane-3β,20β-diol (yield 32%). Crystallization is carried out from ethyl acetate.

Melting point m.p.=196° C.

IR spetrum (Nujol)ν=3600 to 2100, 1585, 1030 cm$^{-1}$

EXAMPLE 3

14α-Amino-5β-pregnane-3β,20α-diol

The procedure indicated in Example 1 is followed. The desired product is isolated from its 14β-amino-5β-pregnane-3α,20α-diol isomer by chromotagraphy, on a silica column, of the mother liquors from crystallization of the main product. Crystallization is carried out from a mixture of ethyl acetate and methanol. Melting point m.p.=188° C.

EXAMPLE 4

14α-Amino-5β-pregnane-3β, 20α-diol

The procedure of Example 2 is followed. The desired product is isolated by chromtography, on a silica column, of the mother liquors from crystallization of the 14β-amino-5β-pregnane-3β,20β-diol isomer.

The product is crystallized from isopropanol. Melting point m.p.=216° C.

EXAMPLE 5

14β-Amino-5β,17βH-pregnane-3β,20α-diol 0.5 g of 20-oxo-5β,17βH-pregnane-3β,14β-diol is reduced with 120 mg of potassium borohydride in 3 ml of methanol. After the reaction, an acetylation is carried out with axetic anhydride in pyridine, in accordance with the customary techniquies, to give di-O-acetyl-5β, 17βH-pregnane-3β,14β,20α-triol with a yield of 95%.

0.4 g of the diacetyltriol obtained as indicated above is dissolved in 30 ml of a benzene solution of hydrozoic acid, and 0.6 ml of boron trifluoride etherate is then added. After treatment as in Example 1, 0.1 g of lithium aluminum hydride is reacted with the residue in 10 ml of tetrahydrofuran. After hydrolysis, extraction and crystallization from ethyl acetate, 0.25 g (yield 80%) of 14β-amino-5β,17βH-pregnane-3β,20α-diol is obtained.

Melting point m.p.=200°–201° C.

EXAMPLE 6

14β-Amino-5α-pregnane-3β,20α-diol

The procedure of Example 1 is followed using the 5α isomer, the reaction with the boron trifluoride etherate being left to proceed for about 5 hours.

After treatment and reduction with lithium aluminum hydride as in Example 1, the residue is taken up in ethyl acetate and the mixture is then washed with a 10% hydrochloric acid solution. Then, the acetate is removed by evaporation and the acid phases are neutralized with sodium carbonate and extracted with chloroform. After filtration, the filtrate is dried and, after crystallization from ethyl acetate, gives 14β-amino-5α-pregnane-3β,20α-diol with a yield of more than 50%.

Melting point m.p.=246° C.

EXAMPLE 7

14β-Amino-5α-pregnane-3β,20β-diol

The procedure of Example 1 (a) is followed using the 5α isomer of the starting pregnanediol, and the 20β isomer of the diacetyltriol obtained is isolated. the same treatment as in Example 1 (b) is then applied; this gives 14β-amino-5α-pregnane-3β,20β-diol, which is recrystallized from diisopropyl ether.

Melting point m.p.=213° C.

EXAMPLE 8

14β-Amino-21-nor-5β-pregnane-3β,20-diol

This compound is prepared as indicated in Example 6 of French Pat. No. 2,464,270 in the name of the Applicant Company.

EXAMPLE 9

14β-Amino-5β-pregnane-3β,12β,20β-triol 1.1 g of lithium aluminum hydride is added, while keeping the temperature at 0° C., to a solution of 130 ml of tetrahydrofuran containing 8 g of a mixture of 20-oxo-5β-pregnane-3β,12β,14β-triol and corresponding 0-acetylated derivatives, the mixture having been obtained by reacting a solution of methyl-lithium in ether with 3β,12β-diacetoxy-14β-hydroxy-5β-etianic acid in tetrahydrofuran, in the presence of sodium hydride, at a temperature below about 10° C., under a nitrogen atmosphere.

Ethyl acetate is added in the cold, followed by a mixture of tetrahydrofuran and water. After filtration and evaporation of the solvent, 7.6 g of 5β-pregnane-3β,12β,14β,20ε-tetrol are collected in the form of a colorless powder.

The above product is dissolved in 120 ml of methylene chloride, and 9.2 ml of acetic anhydride and 1.2 g of 4-dimethylaminopyridine are added to the solution. The reaction mixture is stirred for a few hours and then washed with a solution of sodium carbonate, and the aqueous phase is extracted with methylene chloride. After drying, 9.3 g of 3,12,20-tri-0-acetyl-5β-pregnane-3β,12β,14β,20ε-tetrol are obtained.

The two isomers 20α and 20β are separated by chromatograpy on Merck H60 silcia using a mixture of methylene chloride and acetone (96.5/3.5) as the eluent.

The 3,12,20-tri-0-acetyl-5β-pregnane-3β,12β,14β,20β-tetrol is recrystallized from ether (melting point m.p.=216° C.). 5.7 g of this product are dissolved in 330 mg of an approximately 10 M benzene solution of hydrozoic acid, 7.3 ml of freshly distilled boron trifluoride etherate are then added and the mixture is stirred for about 25 minutes.

After alkalisation with a mixture of aqueous ammonia and crushed ice, extraction with benzene, washing with water, drying over sodium sulfate and evaporation, 5.8 g of a residue are obtained, which is dissolved in 300 ml of ethanol. The solution is hydrogenated at ambient temperature, under a hydrogen atmosphere, for 48 hours, in the presence of 2.9 g of palladium-on-calcium carbonate (5% strength).

The catalyst is removed by filtration and the filtrate is evaporated to dryness to give 5.5 g of a colorless foam, which is dissolved in toluene.

The solution is washed several times with a 5% strength solution of sulfamic acid. The precipitate formed is filtered off and purified to give 0.5 g of 3, 12,20-tri-0-acetyl-14β-amino-5β-pregnane-3β,12β,20β-triol. The acid aqueous phases are rendered alkaline with sodium carbonate and extracted with methylene chloride to give 0.75 g of the same product.

Melting point m.p.=211° C. (isopropyl ether)

0.2 g of 3,12,20-tri-0-acetyl-14β-amino-5β-pregnane-3β,12β,20β-triol, obtained as indicated above, is saponified in 150 ml of a 1N methanolic solution of sodium hydroxide by stirring the suspension for 2 hours at ambient temperature and then heating it under reflux for 30 minutes.

After the solvent has been evaporated off, the residue is extracted with chloroform. This give 0.15 g of 14β-amino-5β-pregnane-3β,12β,20β-triol, which can be recrystallized from a mixture of ethyl acetate and methanol.

Melting point m.p.=238° C.

IR spectrum (Nujol) ν=3400, 3330, 3270, 3180, 3100, 2660, 1615, 1600 cm$^{-1}$

The 14-aminosteroids according to the invention, represented by the general formula (I) above, possess valuable pharmacological properties and, more particularly, they possess a positive inotropic activity.

These properties, which are illustrated below, show that the 14-aminosteroids of the general formula (I) and also their pharmaceutically acceptable salts can be used in human and veterinary therapy as medicaments for treating cardiac insufficiency.

The toxicological experiments carried out showed that the acute toxicity of the 14-aminosteroids according to the invention was relatively low and, in particular, considerably lower than that of the customary digitalis-based compounds such as digitoxin and digoxin.

The inotropic effect in vitro was demonstrated on isolated guinea-pig heart in accordance with Langendorff's method and on isolated guinea-pig auricle. The results obtained show that the 14-aminosteroids according to the invention can be applied in the treatment of cardiac insufficiency.

By way of example, in the case of 14β-amino-5β-pregnane-3β,12β,20β-triol, the Langendorff test on profused isolated heart shows an approximately 30 to 40% increase in the cardiac output for doses of 1 to 30 μg/ml. In the tests on isolated guinea-pig auricle, for a concentration of 10$^{-5}$g/liter, an approximately 150% increase in the concentration force is found, relative to the control value. These results are confirmed by varying the experimental conditions, after administration of propanolol, proving the direct myocardial action of the compound and dispensing with an adrenergic medication.

Comparaple resuls are obtained with 14β-amino-21-nor-5β-pregnane-3β,20-triol.

The derivatives of the general formula (I) and their pharmaceutically acceptable salts can be administered in the customary forms, the actvie principle being diluted in a suitably chosen, pharmaceutically acceptable carrier, for example in the form of tablets, gelatin cap-coated tablets, suppositories, injectable solutions or syrups.

By way of example, the tablets can be prepared by mixing the derivative of the general formula (I) or one of its salts with one or more solid diluents such as lactose, mannitol, starch, polyvinylpyrolidone, magnesium stearate, talc and the like. If appropriate, the tablets can contain several layers superimposed around a core, in accordance with the usual techniques, inorder to ensure a sustained release or a delayed effect of the active principle. The coating can consist, for example, of one or more layers of polyvinyl acetate, carboxymethylcellulose or cellulose acetophthalate.

The derivative according to the invention can also be administered in the form of a syrup or a solution to be taken orally, which is obtained by dissolving the derivative of the formula (I) or one of its pharmaceutically acceptable salts in water or glycerol, for example, and, if appropriate, incorporating a customary additive such as a sweetner or an antioxidant.

Injectable solutions can be prepared in accordance with the well-known techniques and consist, for example, of a solution containing a derivative of the formula (I) or one of its pharmaceutically acceptable salts dissolved in double-distilled water, an aqueous-alcoholic solution, propylene glycol or the like, or a mixture of these solvents. If appropriate, a suitable additive such as a preservative can be added.

The doses administered are determined by the doctor according to the chosen method of administration, the severity of the complaint treated, the duration of the treatment, and soon. For example, in the case of oral administration to men, the doses can be between 0.005 and 5 mg/kg.

We claim

1. A method for the treatment of cardiac insufficiencies which comprises administering to an afflicted subject a therapeutically effective amount of 14-amino steroid represented by the general formula (I):

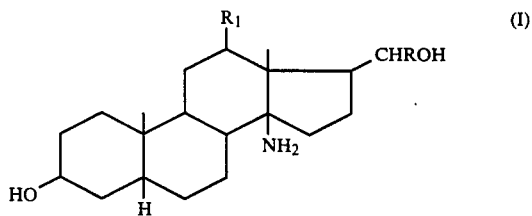

in which R represents a hydrogen atom or a lower alkyl group containing 1 to 4 carbon atoms and R$_1$ represents a hydrogen atom or a hydroxyl group, or a pharmaceutically acceptable salt thereof.

2. A method as claimed in claim 1, in which R is a hydrogen atom or a methyl group.

3. A method as claimed in claim 2, in which the —NH$_2$ group in the 14-position possesses the α configuration.

4. A method as claimed in claim 2, in which the —NH$_2$ group in the 14-position possesses the β configuration.

5. A 14-aminosteroid which is represented by the general formula (I)

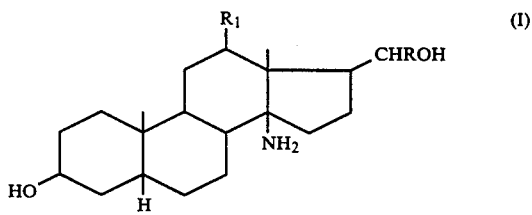

in which R is a hydrogen atom or a lower alkyl group containing 1 to 4 carbon atoms and R$_1$ is a hydrogen atom or a hydroxyl group, R and R$_1$ not geing a hydrogen atom simultaneously, it being understood that when R$_1$ is a hydrogen atom, the —OH group in the 20-position has the β configuration when the —OH group in the 3-position has the β configuration and when the hydrogen atom in the 17-position possesses the α configuration.

6. A 14-aminosteroid as claimed n claim 5, in which R is a methyl group.

7. A process for the preparation of a 14-aminosteroid of the general formula (I):

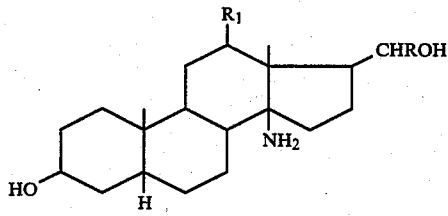

in which R is a hydrogen atom or a lower alkyl group having 1 to 4 carbon atoms and $R_1$ represents a hydrogen atom or hydroxyl group, which comprises reducing and then acetylating a 3,14-hihydroxysteroid of the formula (II):

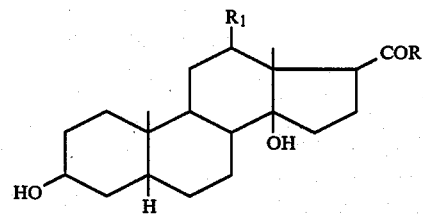

in which R has the dame definition as above, to form an 0-acetylated 3,14,20-trihyrdoxysteroid of the formula (III):

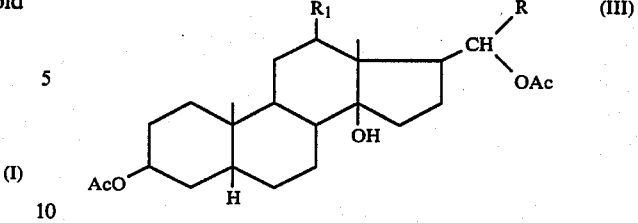

in which R has the same meaning as above, $R_1$ in a hydrogen atom or an acetyl group and Ac is an acetyl group, reacting a hydrozoic acid/boron trifluoride complex with the compound of the formula (III) to form the corresponding 14-azido derivative, and the reducing this with a metal hydride or by catalytic hydrogenation.

8. A pharmaceutical composition for the treatment of cardiac insufficiencies which contains a therapeutically effective amount of a 14-aminosteroid represented by the general formula (I):

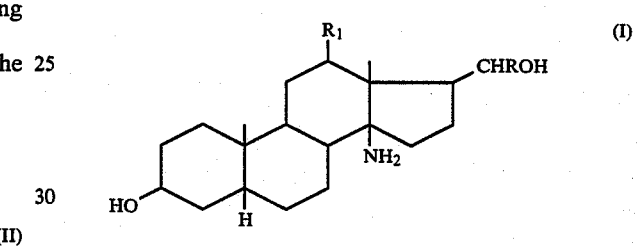

in which R represents a hydrogen atom or a lower alkyl group containing 1 to 4 carbon atoms and $R_1$ represents a hydrogen atom or a hydroxyl group, R and $R_1$ not being a hydrogen atom simultaneously, it being understood that when $R_1$ is a hydrogen atom, the —OH group in the 20-position has the $\beta$ configuration when the —OH group in the 3-position has the $\beta$ configuration and when the hydrogen atom in the 17-position possesses the $\alpha$ configuration or a pharmaceutically acceptable salt thereof, and a pharmaceutically acceptable carrier.

9. A pharmaceutical composition as claimed in claim 8, in which R is a methyl group.

* * * * *